US011369436B2

(12) United States Patent
Kula et al.

(10) Patent No.: US 11,369,436 B2
(45) Date of Patent: Jun. 28, 2022

(54) SYSTEMS AND METHODS FOR DISPLAYING GUIDANCE IMAGES WITH SPATIAL ANNOTATIONS DURING A GUIDED MEDICAL PROCEDURE

(71) Applicant: 7D SURGICAL INC., Toronto (CA)

(72) Inventors: Andrew Kula, Richmond Hill (CA); Elena Berman, Concord (CA); Adrian Mariampillai, Toronto (CA); Peter Siegler, Toronto (CA); Michael Leung, Markham (CA); Beau Anthony Standish, Toronto (CA); Victor X. D. Yang, North York (CA)

(73) Assignee: 7D SURGICAL ULC, Toronto (CA)

( * ) Notice: Subject to any disclaimer, the term of this patent is extended or adjusted under 35 U.S.C. 154(b) by 922 days.

(21) Appl. No.: 15/404,432

(22) Filed: Jan. 12, 2017

(65) Prior Publication Data

US 2017/0202626 A1 Jul. 20, 2017

Related U.S. Application Data

(60) Provisional application No. 62/279,412, filed on Jan. 15, 2016.

(51) Int. Cl.
*A61B 34/20* (2016.01)
*A61B 34/00* (2016.01)
*A61B 17/17* (2006.01)

(52) U.S. Cl.
CPC .............. *A61B 34/20* (2016.02); *A61B 34/25* (2016.02); *A61B 17/1757* (2013.01); *A61B 2034/2055* (2016.02)

(58) Field of Classification Search
CPC ............ A61B 34/20; A61B 2034/2055; A61B 17/1757; A61B 90/37; A61B 2034/107; A61B 34/25; A61B 8/0841
See application file for complete search history.

(56) References Cited

U.S. PATENT DOCUMENTS

| 6,470,207 | B1 * | 10/2002 | Simon ..................... G06F 19/00 600/426 |
| 9,076,246 | B2 * | 7/2015 | Ma ........................... G06T 7/33 |
| 9,510,771 | B1 * | 12/2016 | Finley .................... A61B 5/743 |
| 9,848,922 | B2 * | 12/2017 | Tohmeh ............. A61B 17/7083 |
| 2009/0171184 | A1 * | 7/2009 | Jenkins .................. A61B 5/055 600/411 |
| 2010/0100909 | A1 * | 4/2010 | Arsenault .......... H04N 21/8166 725/70 |
| 2011/0137156 | A1 * | 6/2011 | Razzaque .......... A61B 18/1477 600/424 |
| 2014/0148808 | A1 * | 5/2014 | Inkpen ............... A61B 17/1703 606/80 |
| 2016/0100909 | A1 * | 4/2016 | Wollowick ................ G06T 7/33 600/424 |
| 2016/0113728 | A1 * | 4/2016 | Piron ................... A61B 5/0062 606/130 |

* cited by examiner

*Primary Examiner* — Lynsey C Eiseman
*Assistant Examiner* — Amanda L Steinberg
(74) *Attorney, Agent, or Firm* — Hill & Schumacher

(57) ABSTRACT

The present disclosure provides systems and methods for generating spatial annotations within guidance images that are displayed during a guided medical procedure, where the spatial annotations provide spatial graduations indicating known length measures. The spatial measures may be employed to visually assess the sizes of anatomical and/or functional features displayed in the guidance images.

26 Claims, 10 Drawing Sheets

SYSTEMS AND METHODS FOR DISPLAYING GUIDANCE IMAGES WITH SPATIAL ANNOTATIONS DURING A GUIDED MEDICAL PROCEDURE

CROSS-REFERENCE TO RELATED APPLICATION

This application claims priority to U.S. Provisional Application No. 62/279,412, titled "SYSTEMS AND METHODS FOR DISPLAYING GUIDANCE IMAGES WITH SPATIAL ANNOTATIONS DURING A GUIDED MEDICAL PROCEDURE" and filed on Jan. 15, 2016, the entire contents of which is incorporated herein by reference.

BACKGROUND

The present disclosure relates to systems and methods that perform tracking of medical instruments during a navigated medical procedure.

Pedicle screw implantation has become a relatively common procedure to support a number of degenerative or acute clinical conditions of the spine. A number of pre-planning software systems have been developed to aid the implantation of these screws, predominantly by allowing the surgeon to size the width and length of screws that will be implanted during the surgery. However, screw sizes determined prior to the surgery are typically selected assuming ideal conditions such as optimal entry points and trajectory. If, during the surgery, these entry points and trajectories are not exactly matched, the screw size selected prior to surgery may not be optimal.

SUMMARY

The present disclosure provides systems and methods for generating spatial annotations within guidance images that are displayed during a guided medical procedure, where the spatial annotations provide spatial graduations indicating known length measures. The spatial measures may be employed to visually assess the sizes of anatomical and/or functional features displayed in the guidance images.

Accordingly, in a first aspect, there is provided a method of performing tracking and navigation during a medical procedure, the method comprising:

detecting, with a tracking system, signals from one or more fiducial markers associated with a medical instrument, the medical instrument comprising an elongate portion characterized by a longitudinal axis;

processing the signals to determine a position and an orientation of the medical instrument;

employing a coordinate transformation to represent pre-operative image data and the position and orientation of the medical instrument within a common reference frame; and generating and displaying navigation images comprising:
a virtual representation of the medical instrument;
anatomical and/or functional features associated with the pre-operative image data; and
a plurality of spatial annotations positioned at prescribed locations along the longitudinal axis relative to the position of the medical instrument, wherein each spatial annotation identifies a respective image region having a known length measure associated therewith, and wherein each spatial annotation is configured such that the image region associated therewith is centered on the longitudinal axis and extends orthogonal to the longitudinal axis;

each spatial annotation thereby enabling a visual assessment of the size of anatomical and/or functional features proximal to the longitudinal axis.

In another aspect, there is provided a system for performing tracking and navigation during a medical procedure, the system comprising:

a tracking system for tracking the position and orientation of a medical instrument, the medical instrument comprising an elongate portion characterized by a longitudinal axis; and computer hardware operatively connected to said tracking system, wherein said computer hardware is configured to:

employ a coordinate transformation to represent pre-operative image data and the position and orientation of the medical instrument within a common reference frame; and generate and display navigation images comprising:
a virtual representation of the medical instrument;
anatomical and/or functional features associated with the pre-operative image data; and
a plurality of spatial annotations positioned at prescribed locations along the longitudinal axis relative to the position of the medical instrument, wherein each spatial annotation identifies a respective image region having a known length measure associated therewith, and wherein each spatial annotation is configured such that the image region associated therewith is centered on the longitudinal axis and extends orthogonal to the longitudinal axis;

each spatial annotation thereby enabling a visual assessment of the size of anatomical and/or functional features proximal to the longitudinal axis.

In another aspect, there is provided a method of performing tracking and navigation during a medical procedure, the method comprising:

detecting, with a tracking system, signals from one or more fiducial markers associated with a medical instrument, the medical instrument comprising an elongate portion characterized by a longitudinal axis;

processing the signals to determine a position and an orientation of the medical instrument;

employing a coordinate transformation to represent pre-operative image data and the position and orientation of the medical instrument within a common reference frame; and generating and displaying navigation images comprising:
anatomical and/or functional features associated with the pre-operative image data; and
a spatial annotation positioned at a discrete location along the longitudinal axis relative to the position of the medical instrument, wherein the spatial annotation identifies a respective image region having a known length measure associated therewith, and wherein the spatial annotation is configured such that the image region associated therewith is centered on the longitudinal axis and extends orthogonal to the longitudinal axis;

the spatial annotation thereby enabling a visual assessment of the size of anatomical and/or functional features proximal to the longitudinal axis.

In another aspect, there is provided a method of performing tracking and navigation during a medical procedure, the method comprising:

detecting, with a tracking system, signals from one or more fiducial markers associated with a medical instrument, the medical instrument comprising an elongate portion characterized by a longitudinal axis;

processing the signals to determine a position and an orientation of the medical instrument;

employing a coordinate transformation to represent pre-operative image data and the position and orientation of the medical instrument within a common reference frame; and
generating and displaying navigation images comprising:
anatomical and/or functional features associated with the pre-operative image data; and
a plurality of spatial annotations positioned at prescribed locations along the longitudinal axis relative to the position of the medical instrument, wherein each spatial annotation identifies a respective image region having a known length measure associated therewith, and wherein each spatial annotation is configured such that the image region associated therewith is centered on the longitudinal axis and extends orthogonal to the longitudinal axis;
each spatial annotation thereby enabling a visual assessment of the size of anatomical and/or functional features proximal to the longitudinal axis.

In another aspect, there is provided a method of performing spatial annotations during a guided medical procedure, the method comprising:
generating and displaying navigation images comprising:
a virtual representation of a medical instrument tracked during the medical procedure, the medical instrument comprising an elongate portion characterized by a longitudinal axis;
anatomical and/or functional features associated with pre-operative image data, wherein the pre-operative image data and the position and orientation of the medical instrument are known in a common reference frame; and
a plurality of spatial annotations positioned at prescribed locations along the longitudinal axis relative to the position of the medical instrument, wherein each spatial annotation identifies a respective image region having a known length measure associated therewith, and wherein each spatial annotation is configured such that the image region associated therewith is centered on the longitudinal axis and extends orthogonal to the longitudinal axis;
each spatial annotation thereby enabling a visual assessment of the size of anatomical and/or functional features proximal to the longitudinal axis.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
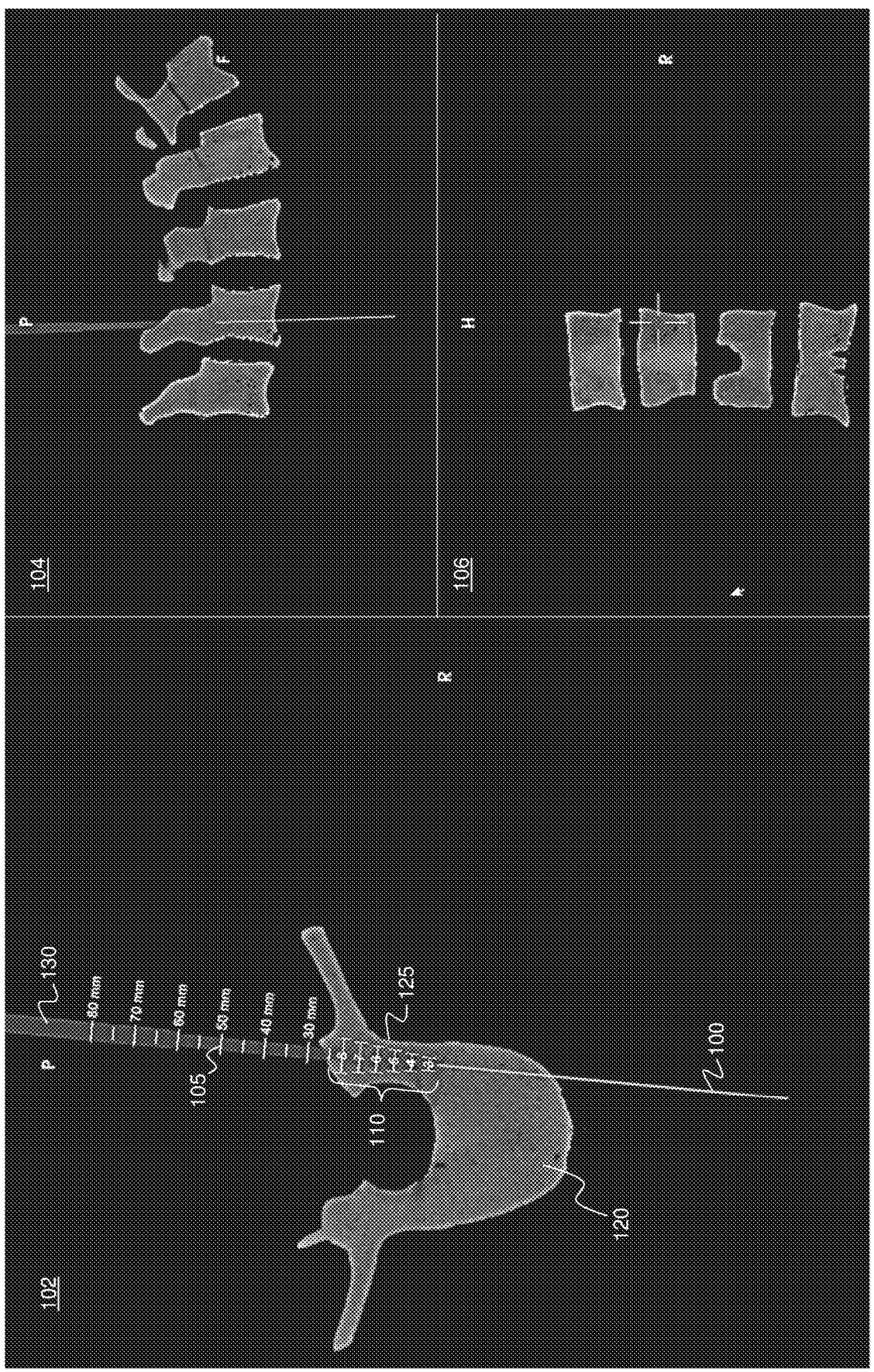
FIGS. 1A and 1B are screenshots of an example user interface that displays two-dimensional guidance images having spatial annotations indicating image regions having known length measures.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure provide systems and methods for generating and displaying spatial annotations in guidance images that are displayed during a guided medical procedure, where the spatial annotations provide spatial graduations indicating known length measures. Such spatial measures may then be employed to visually assess the sizes of anatomical and/or functional features displayed in the guidance images.

According to various example embodiments, the spatial annotations are displayed relative to the position and orientation of a medical instrument that is intraoperatively tracked during a medical procedure, such that the locations of the spatial annotations within the guidance images vary dynamically with the position and orientation of the tracked medical instrument. The tracked medical instrument then may be employed as a dynamic ruler as it is moved relative to the anatomy of the subject.

In some embodiments, the tracked medical instrument has an elongate portion (e.g. a shaft, handle, or other elongate feature) that is characterized by a longitudinal axis. The spatial annotations may then be displayed along the longitudinal axis of the medical probe, such that the spatial annotations provide dynamic graduations that "move" relative to anatomical and/or functional features shown in the navigation image as the medical instrument is moved relative to (e.g. toward, into, within) the tissue of the subject.

Referring now to FIG. 1A, an example of a guidance user interface is shown, where the a set of guidance images 102, 104 and 106 are generated to provide spatial guidance during a medical procedure involving a medical instrument having elongate portion that is characterized by a longitudinal axis 100. The medical procedure of the present non-limiting example involves the insertion of a pedicle screw through the pedicle shown at 125, and the guidance images 102, 104 and 106 show the position and orientation of a pedicle probe 130, as tracked by a tracking system (this portion of the medical procedure occurs prior to the insertion of the pedicle screw).

In the present example illustrate in FIG. 1A, the guidance image 102 shows a two-dimensional cross-section through the spinal column 120, where the two-dimensional image includes, and shows, the longitudinal axis 100 of the medical instrument, as per the typical reslicing of DICOM image data along the longitudinal axis. A plurality of spatial annotations 110 are generated along the longitudinal axis 100 of the medical probe, where each spatial annotation is centered on the longitudinal axis 100. In the present example embodiment, the spatial annotations 110 are generated such that the image region (linear segment) associated with each spatial annotation extends relative to the longitudinal axis 100 in a direction that is perpendicular to the longitudinal axis.

Each spatial annotation delineates (indicates) an image region (in this case, a linear image segment) that has a known length measure associated therewith. Each spatial annotation thus provides a graduation that enables the operator/user to obtain a visual measure of the relative size of anatomical and/or functional features in the guidance images.

The anatomical features may be, for example, various tissue structures that are pre-operatively (or intra-operatively) imaged according to a wide variety of imaging modalities. Examples of functional features include, but are not limited to, activation maps obtained during pre-operative functional magnetic resonance imaging, and diffusion maps obtained during pre-operative diffusion-weighted magnetic resonance imaging, real-time ultrasound which may include functional blood flow (Color/Power Doppler) imaging and/or shear wave imaging.

In some example implementations, as shown in FIG. 1, two or more graduations 105 may be displayed along the longitudinal axis, in order to enable measurements of distances along the longitudinal axis. The graduations 105 may be fixed relative to the position and orientation of the medical instrument 130, such that they follow the medical instrument 130 as the medical instrument is moved relative to anatomical and/or functional features shown in the guidance images.

The length measures associated with the spatial annotations may be displayed in the guidance images. For example, the length measures may be provided in a legend (see, for example, FIGS. 2A-2E). In another example implementation, the length measures may be displayed adjacent to their respective spatial annotations.

As noted above, the two-dimensional image shown in view 102 of FIG. 1A is generated such that the longitudinal axis 100 of the medical instrument, as determined via dynamic tracking of the position of the orientation of the medical instrument, lies within the two-dimensional image. The inclusion of the longitudinal axis 100 within the guidance image ensures that the spatial annotations represent length measures that lie within the guidance image, such that that each length measure represents is not spatially distorted via projection. It is noted that the slicing of DICOM image data along the longitudinal axis will result in the longitudinal axis being present in two of the orthogonal image slices. However, it will be understood that in some implementations, the two-dimensional slice may not fully encompass the longitudinal axis, provided that the longitudinal axis lies with sufficient proximity to the image region including the spatial annotations, such that the spatial annotations represent correct length measures within a prescribed tolerance upon projection onto the image plane, such as a tolerance within ±1, within ±2, within ±5, or within another suitable value as per the clinical requirements. In such implementations, the guidance image may include a projection of the longitudinal axis and the spatial annotations, and the spatial annotations may optionally be represented as having a spatial extent that compensates for the projection error.

FIG. 1A illustrates an example embodiment in which the spatial annotations are spatially arranged along the longitudinal axis in an ordered configuration with respect to the length of their respective known length measures. Accordingly, in some embodiments, the spatial annotations may be displayed in an ordered configuration along the longitudinal axis according to an increasing or decreasing size of the respective known length measures. In one example implementation, the spatial annotations are spatially ordered such that the spatial annotation having the largest known length measure is displayed nearest to a proximal end of the medical instrument (as shown in FIG. 1A).

In the example embodiment shown in FIG. 1A, the spatial annotations are displayed such that they reside along the elongate portion of the medical instrument 130. The spatial annotations may be displayed such that the distalmost spatial annotation is displayed adjacent to the distal end of the medical instrument, as also shown in FIG. 1A.

These example embodiments (involving the display of the spatial annotations along the elongate portion of the medical instrument) may be beneficial when the medical instrument is employed such that a substantial portion (e.g. greater than 5%, 10%, 15%, 20%, or 25%) of the elongate portion of the medical instrument is inserted within the tissue during the medical procedure. For example, as shown in FIG. 1A, the pedicle probe 130 has a distal region that is inserted within the pedicle region of a spinal level, and the display of the spatial annotations along the elongate portion of the pedicle probe causes the spatial annotations to pass through the pedicle as the pedicle probe is inserted, along its longitudinal axis. The operator or user (e.g. a surgeon) observing the guidance images may therefore determine a measure or estimate of the pedicle width by watching the various spatial annotations pass through the pedicle region as the pedicle probe is inserted, and identifying the spatial annotation that best approximates the pedicle width (e.g. passes closest to the minimum observable width of the pedicle). The passage of the spatial annotations through the pedicle region may also be beneficial in allowing an operator to observe any deviations of the pedicle probe from a central axis passing through the center of the pedicle.

The example embodiment illustrated in FIG. 1A may additionally or alternatively be employed by an operator to select a suitable pedicle screw for use during the medical procedure. For example, in some cases, a pedicle screw that is to be employed in a surgical procedure may be available in a plurality of sizes, and at least a subset of the spatial annotations may be displayed such that their respective known length measures correspond to standard screw diameters. In such an embodiment, an operator may select a suitable standard screw size by identifying the spatial annotation that has a desired diameter relative to the width of the pedicle. Accordingly, in general, in some embodiments, at least a subset of spatial annotations are selected such that their respective known length measures corresponding to standard diameters of a tool (e.g. a fastener; where the tool is other than the medical instrument) that is employed during a medical procedure. In some example implementations, a tool such as a pedicle screw may be configured to be expandable to a user-controlled diameter, and the example embodiments disclosed herein may be employed for the determination of a suitable outer diameter when expanding the tool.

In another example embodiment, a subset of spatial annotations may be displayed such that they reside along the elongate portion of the medical instrument 130, while a remainder of the spatial annotations may be displayed in a region along the longitudinal axis that lies beyond (distalward to) the distal end of the medical probe.

Figure 1B:
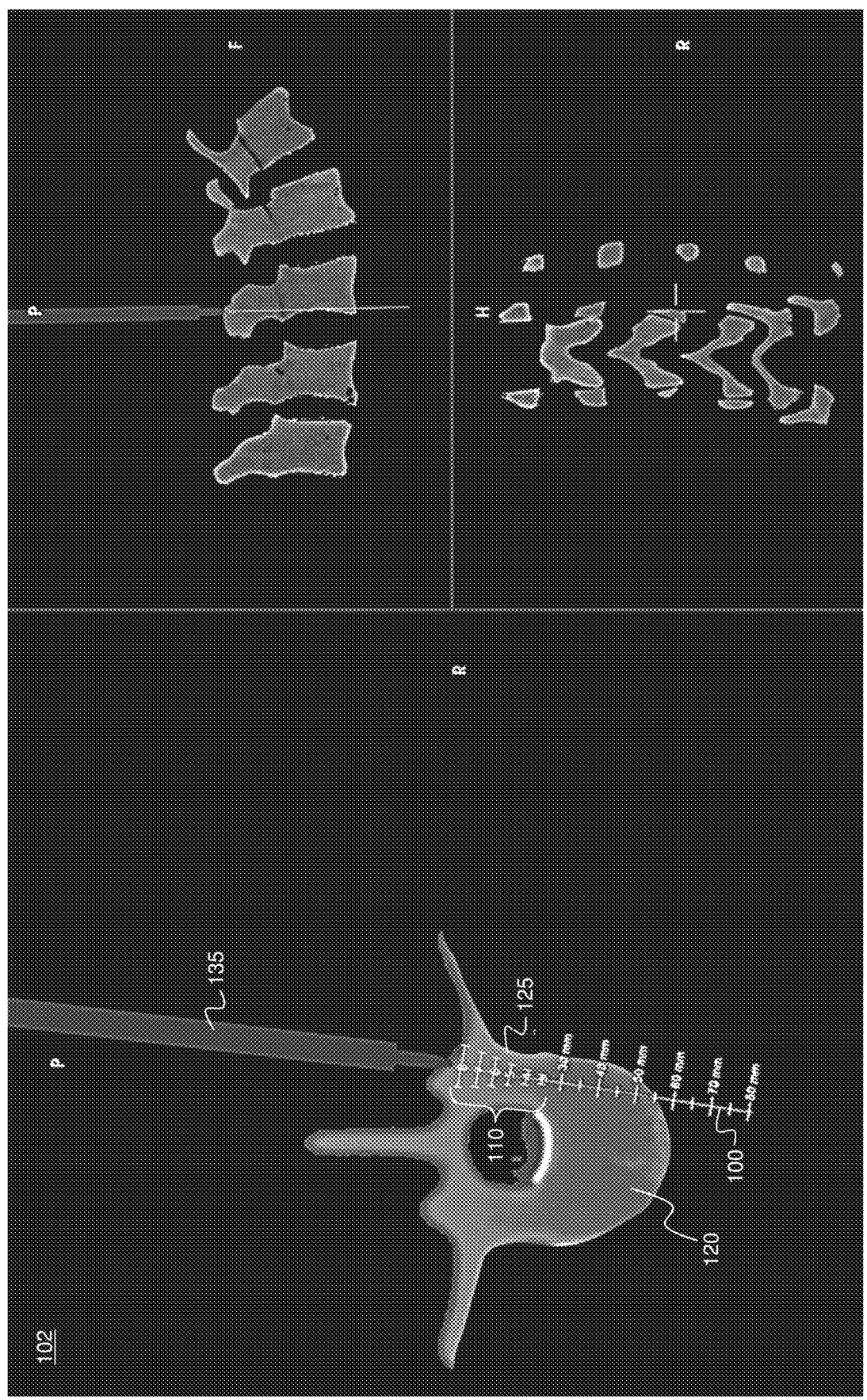

In yet another example embodiment, all of the spatial annotations may be displayed such that they are displayed in a region along the longitudinal axis that lies beyond (distalward to) the distal end of the medical probe. An example of such an embodiment is shown in FIG. 1B, which shows a guidance user interface including a set of guidance images 102, 104 and 106, in which the medical instrument displayed in the guidance images is an awl 135. In the example case of a spinal procedure involving the placement of a pedicle screw, the awl 135 is employed during an initial portion of the procedure in order to select an entry point create an initial path within the cortical region of the bone. Since the awl 135 is only used for entering the cortical bone region, the awl does not penetrate deep into the tissue. Accordingly, in order to generate spatial annotations that are suitable for the measurement or estimation of the pedicle width during the use of the awl 135, the spatial annotations 110 should be projected forward along the longitudinal axis 100, as shown in FIG. 1B, such that the spatial annotations 110 lie in the pedicle region 125 that is distalward relative to the distal end of the awl 135.

Accordingly, in some example embodiments, the spatial annotations may be displayed such that they are projected forward in a distalward direction along the longitudinal axis relative to the distal end of the medical instrument (e.g. distalward from the distal tip of an awl), such when the distal end of the medical instrument contacts an external tissue surface (e.g. the outer surface of a bone) surface at a suitable entry point associated with the medical procedure, each spatial annotation is displayed proximal to a subregion of interest (e.g. overlapping or nearby to a central portion of the pedicle). The spatial offsets between the distal end of the medical instrument and the spatial annotations may be selected, for example, based on a reference atlas, optionally according to the age and/or gender of the subject. Alternatively, the spatial offsets may be determined and configured based on pre-operative images of the subject.

In one example embodiment, the various spatial annotations associated with a medical instrument that is configured to contact external tissue without deeply penetrating the tissue (e.g. an awl, e.g. such that the portion of the elongate body of the medical instrument that penetrates the tissue is less than 5%, less than 10%, less than 15%, less than 20%, or less than 25%) may be projected distalward relative to the distal end of the medical probe and arranged with a higher spatial density, along the longitudinal axis, relative to the density of the spatial annotations that are displayed for a medical instrument that is configured to substantially penetrate the tissue (e.g. such that the portion of the elongate body of the medical instrument that penetrates the tissue is greater than 5%, 10%, 15%, 20%, or 25%). The higher density (along the longitudinal axis) of the spatial annotations that are projected forward may be beneficial for clustering the spatial annotations nearby an anatomical and/or functional region of interest when the medical probe contacts the external tissue.

Although the example implementation shown in FIG. 1A involves the display of a plurality of spatial annotations, in other example embodiments, a single spatial annotation may be shown. For example, a single spatial annotation may be displayed at a discrete location along the longitudinal axis. In some example implementation in which the spatial annotation is employed to select the width of a tool that is to be employed during a subsequent phase of the medical procedure, the spatial annotation may be displayed at a discrete location along the longitudinal axis, such that an axial extent of the spatial annotation, along the longitudinal axis, is substantially less (e.g. less than 50%, less than 25%, less, than 20%, less than 15%, less than 10%, or less than 5%) than the axial length of the tool. This results in the display of a spatial annotation that avoids occluding the guidance image, in stark contrast to methods involving the rendering of a visualization of the tool that involve the display of the full spatial extent of the tool.

It is noted that although the two-dimensional images shown in the preceding embodiments involve planar image slices, in other example implementations involving two-dimensional guidance images, other geometrical image configurations be rendered, such as two-dimensional surfaces having a cylindrical curvature, where the cylindrical surface is selected such that the longitudinal axis lies within the rendered two-dimensional image.

Figure 2A:
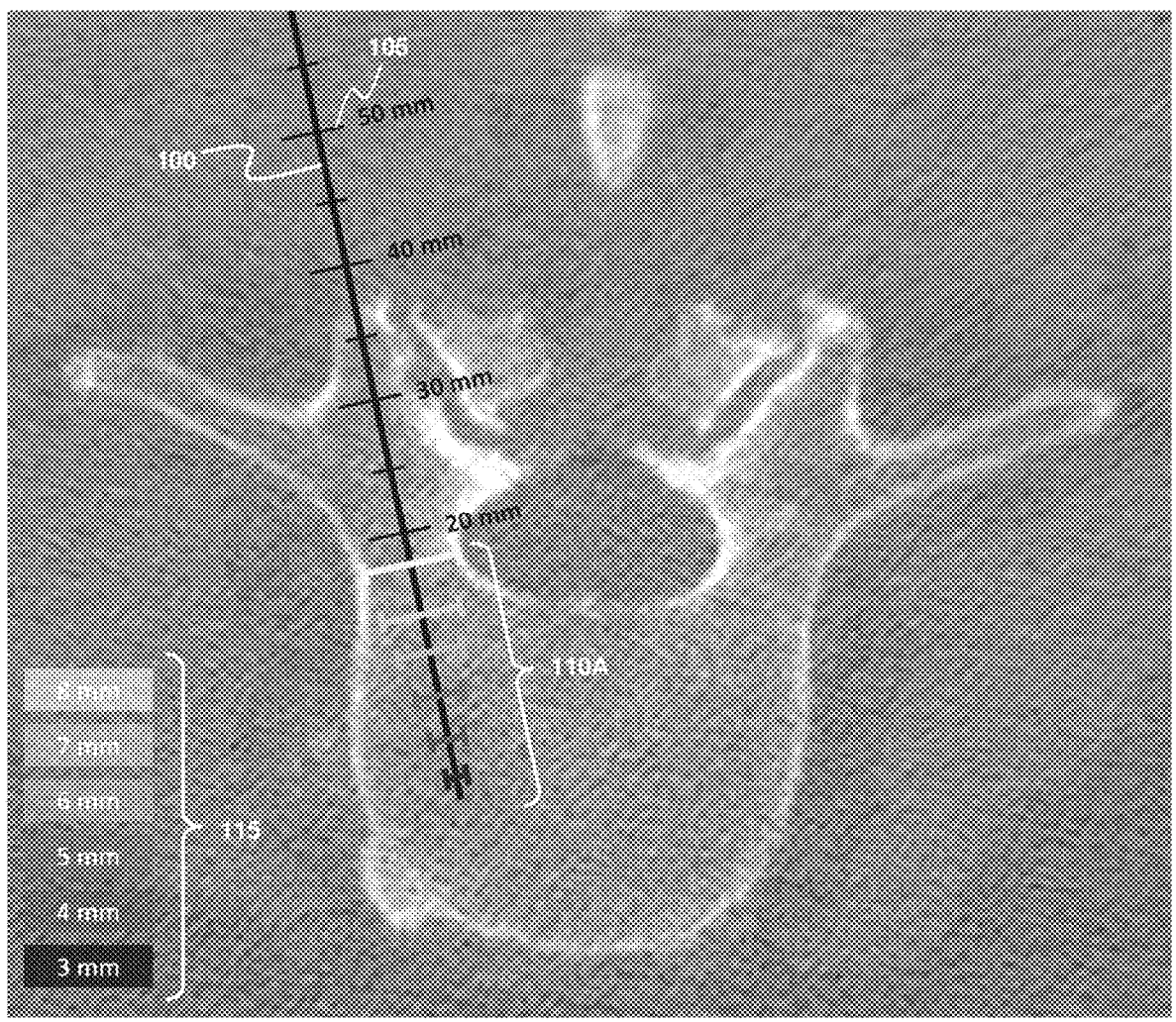
FIGS. 2A-2E illustrate examples of different types of spatial annotations that may be displayed.
Figure 2B:
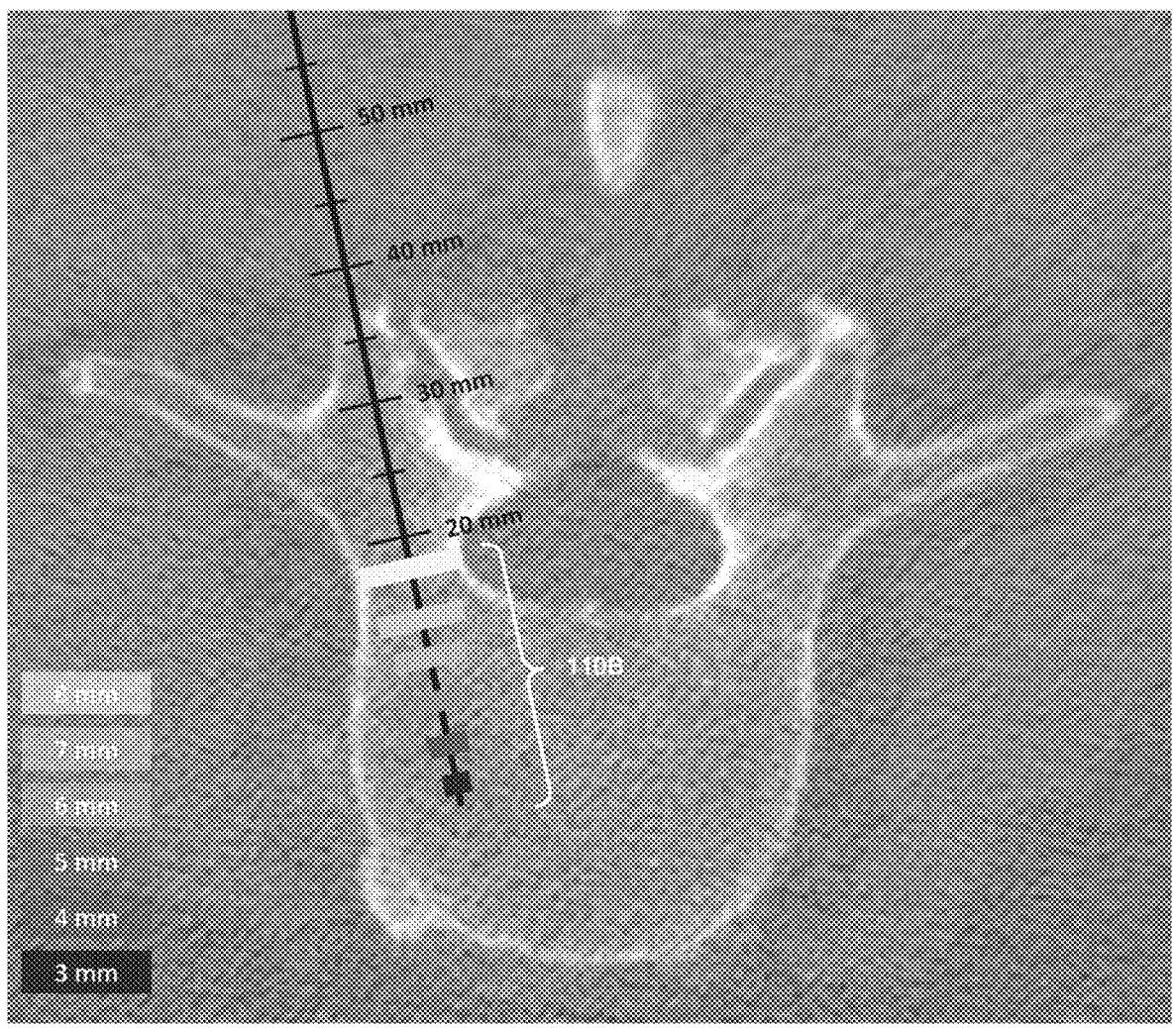
Figure 2C:
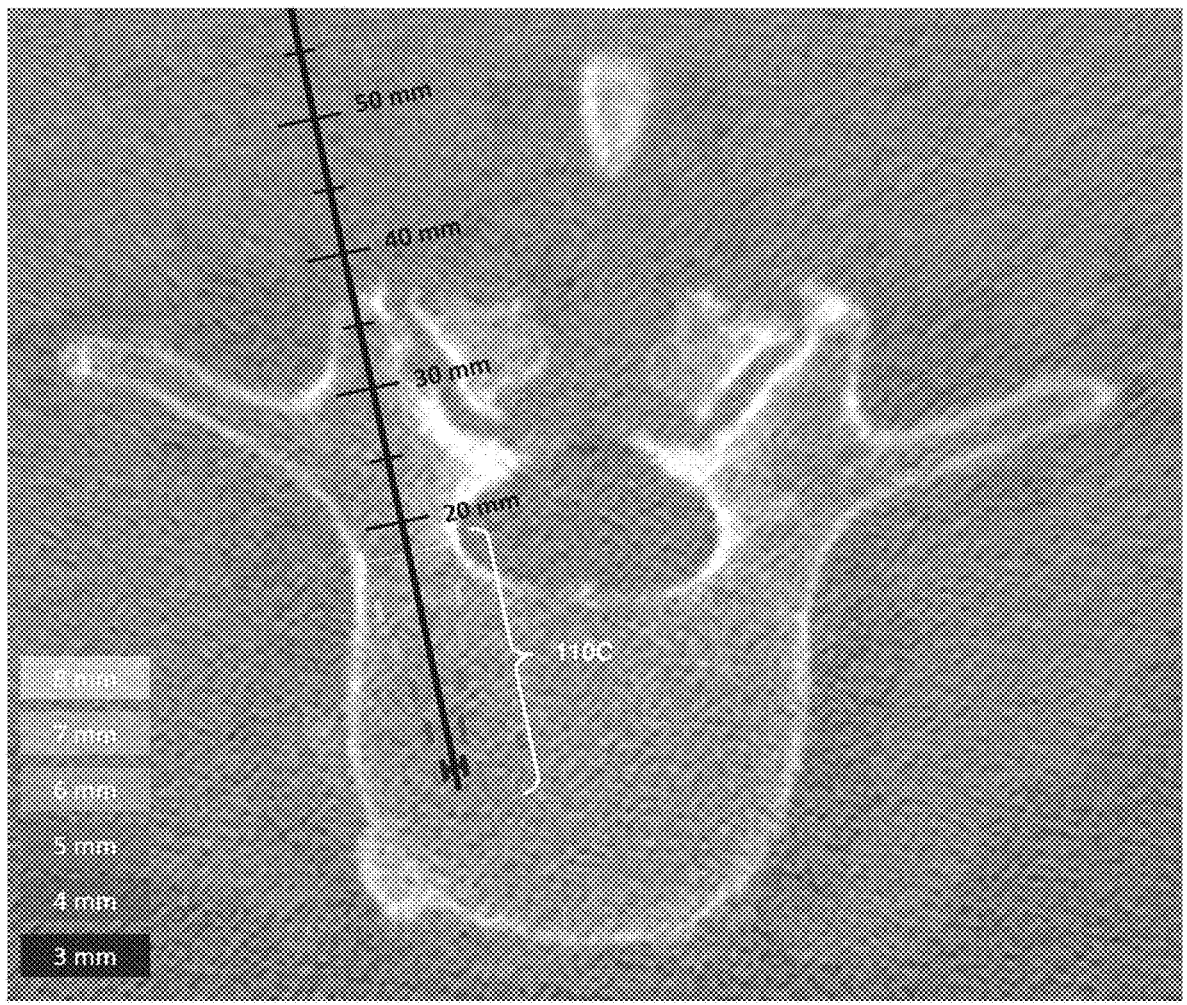
Figure 2D:
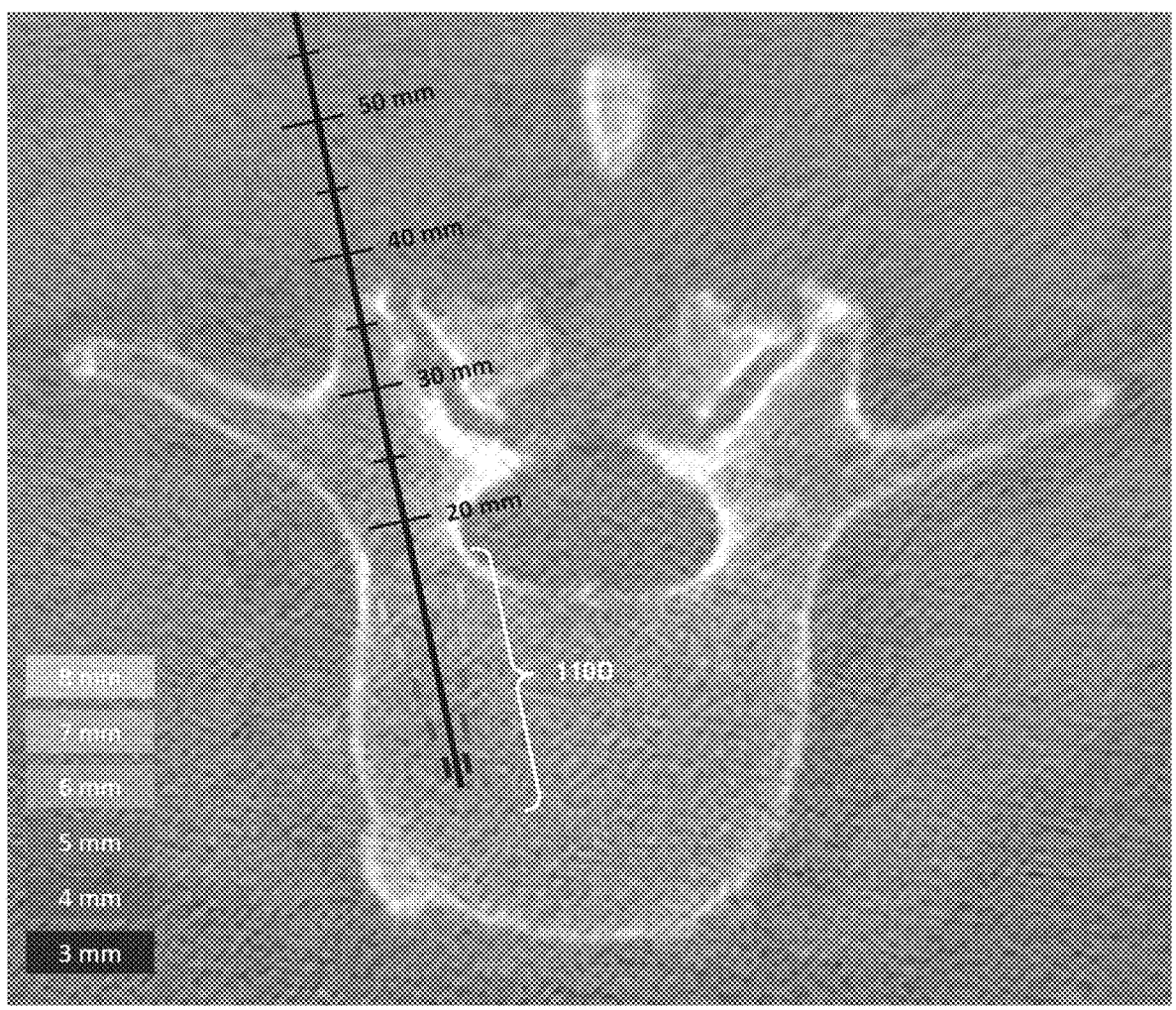
Figure 2E:
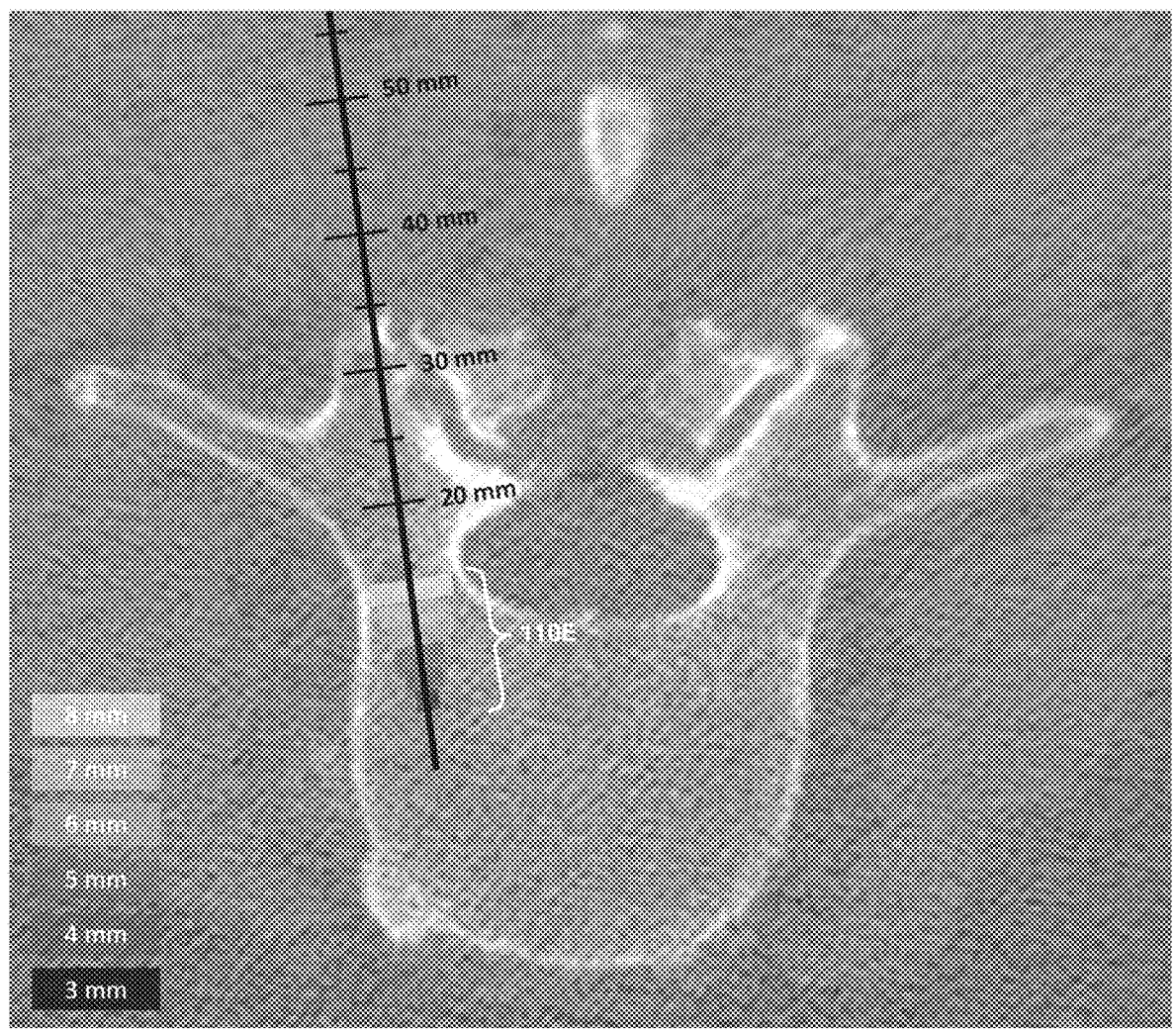

Referring now to FIG. 2A, an example guidance image is shown illustrating a specific example of a set of spatial annotations 110A that are displayed along the longitudinal axis 100. The figure also shows a legend 115 that correlates each spatial annotation with its respective known length measure. Also shown in the figure are the optional axial graduations 105 that enable length measurements along the longitudinal axis 100. It is noted that the medical instrument is not shown in the guidance image, but in various clinical implementations of the methods and systems disclosed herein, it may be preferable to display a visual representation of the tracked medical instrument in the guidance image (e.g. as in FIGS. 1A and 1B). FIGS. 2B-2E illustrate additional non-limiting examples of different types of spatial annotations (110B-110E) that may be employed to identify image regions. It will be understood that the example spatial annotations provided in FIGS. 2A-2E are merely illustrative in nature, and that a wide variety of types and geometries of spatial annotations may be employed without departing from the intended scope of the present disclosure. For example, although the spatial annotations are shown according to different grayscale levels, the spatial annotations may be shown in different colours.

Figure 3:
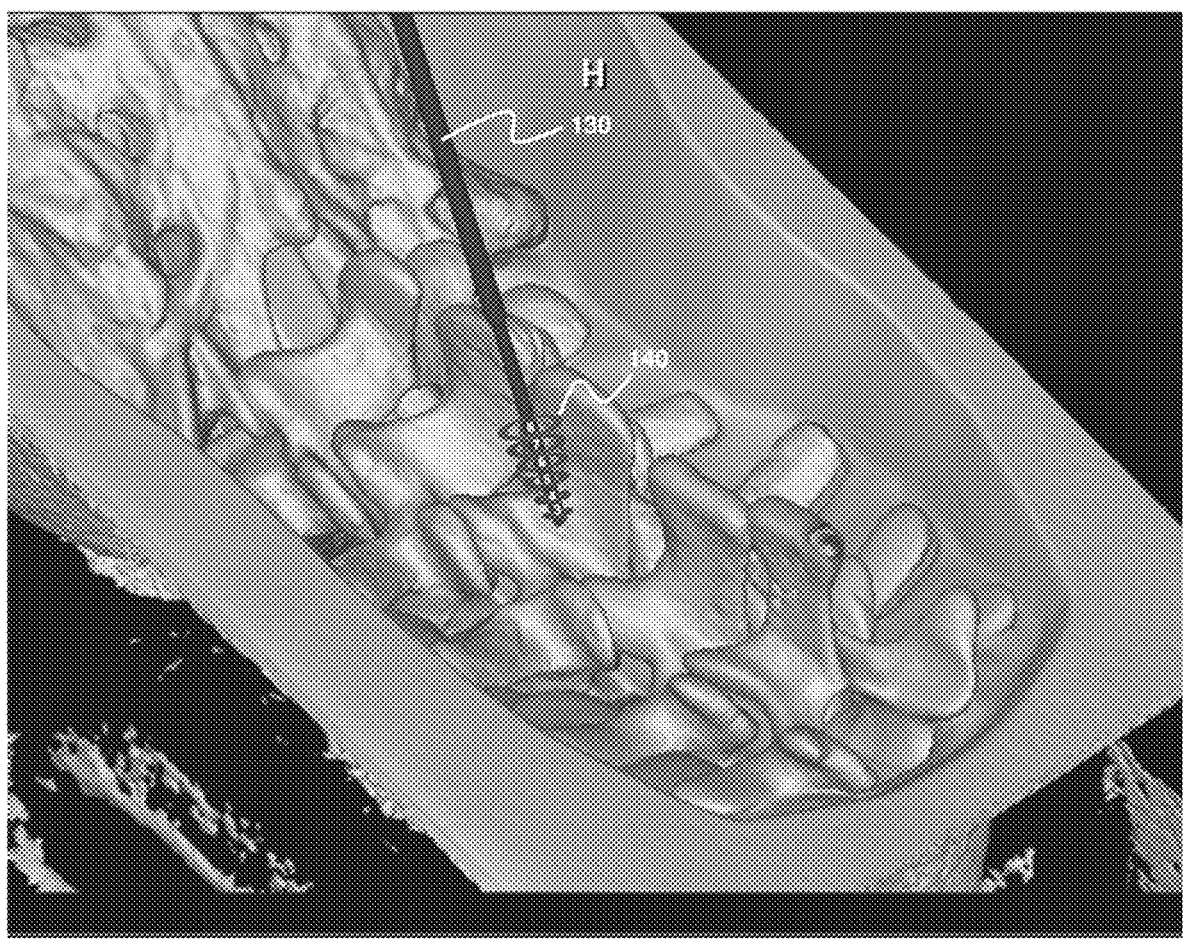
FIG. 3 provides an example of a three-dimensional image having spatial annotations indicating image regions having known length measures.

Although the examples embodiments that were described with reference to FIGS. 1A-1B and 2A-2E pertain to the display of two-dimensional images, it will be understood that the embodiments disclosed herein may be adapted to three-dimensional images, such as two-dimensional representations of three-dimensional images, virtual reality based renderings, and holographic images. In cases in which the navigation image is configured to display a volumetric region, each spatial annotation may be generated to identify a spatial region surrounding the longitudinal axis. For example, a spatial annotation may be generated as a circular shape surrounding the longitudinal axis, such as a ring or a disc (or one or more portions thereof). FIG. 3 illustrates an example implementation of a three-dimensional navigation image that shows the positioning of a pedicle probe 130 relative to the three-dimensional surface of the spinal region, where a set of ring-shaped spatial annotations 140 are distributed along the longitudinal axis of the pedicle probe. Additionally, to improve visibility of the annotations when the medical instrument is inserted into the tissue or when the distalward projection lies within the 3D tissue volume it is possible to apply different transparency values to the 3D anatomical data.

Figure 4:
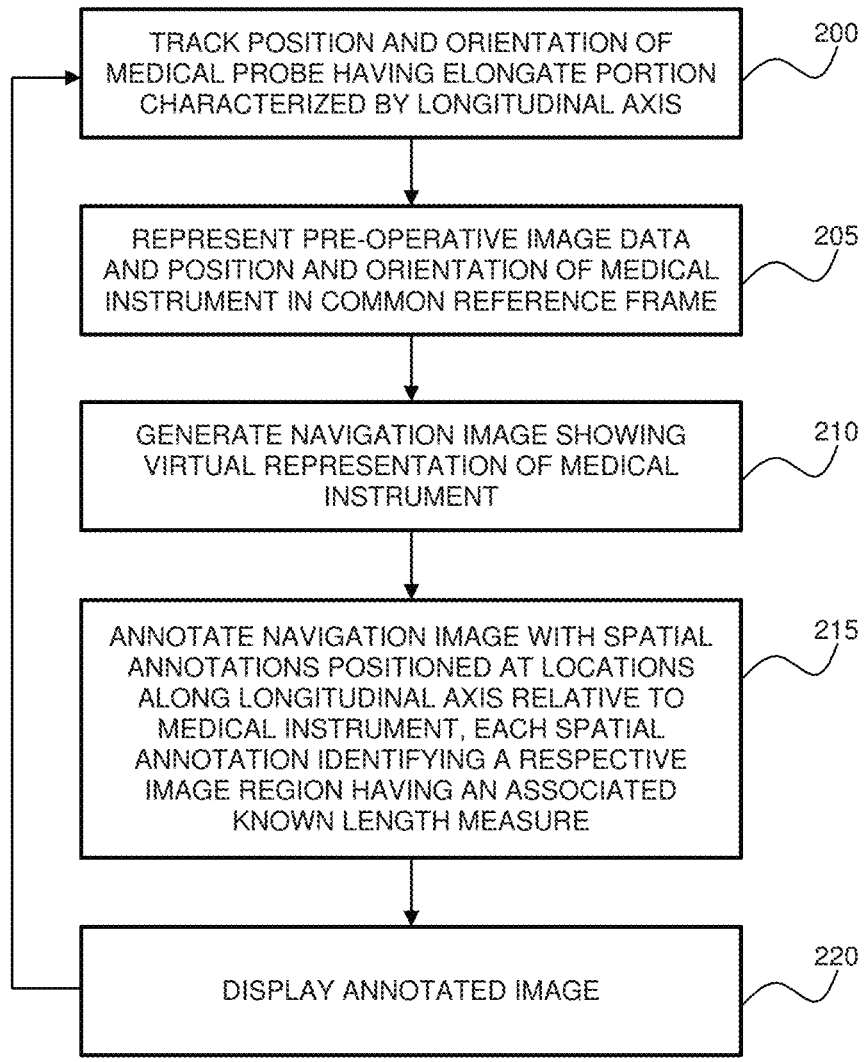
FIG. 4 is a flow chart illustrating an example method of performing tracking and navigation during a medical procedure, in which guidance images are generated such that spatial annotations indicating image regions having known length measures are displayed relative to the tracked position and orientation of a tracked medical instrument.

Referring now to FIG. 4, and flow chart is provided that illustrates an example method of performing tracking and navigation during a medical procedure. In step 200, the position and orientation of the medical instrument (having an elongate portion characterized by a longitudinal axis) are tracked. As noted above, this may be achieved using a tracking system that detects signals from one or more fiducial markers associated with (e.g. provided on or attached to) the medical instrument, and the detected signals may be processed to determine the position and orientation of the medical instrument. A fiducial marker may be active or passive, and may be detectable using an optical detector. An example optical passive marker is a reflective sphere, or portion thereof, and an example active optical marker is an LED. Another example of a marker is a glyph, which may contain sufficient spatial and/or geometrical co-planar features for determining a three-dimensional position and orientation. For example, a glyph marker may include at least three corner features, where the three corner features define a plane. In an alternative example embodiment, the position and orientation of a medical instrument may be tracked via the detection of a surface profile of at least portion of the medical instrument, or structure attached thereto.

In step 205, pre-operative image data, and the tracked position and orientation of the medical instrument, are expressed in a common reference frame, such as an intraoperative reference frame (e.g. a reference frame associated with a tracking system, or a reference frame associated with the patient, such as a reference frame associated with stereotactic frame attached to the subject). This may be performed, for example, by employing any suitable registration method involving the registration of the pre-operative image data to an intraoperative reference frame. Example methods include the use of pre-operative and intraoperative fiducial markers, with optional intraoperative identification of the markers via a tracked instrument. Alternative methods include the intraoperative detection of an anatomical surface (e.g. via structured light detection or other surface detection modalities) and the registration of the detected surface with a surface data obtained via the surface segmentation of pre-operative volumetric surface data. Example image registration methods are described in U.S. Pat. No. 9,119,670, titled "SYSTEM AND METHODS FOR INTRAOPERATIVE GUIDANCE FEEDBACK", filed on Oct. 31, 2012, which is incorporated herein by reference in its entirety, and in International PCT Patent Application No. PCT/CA2014/051120, titled "SYSTEM AND METHOD FOR GENERATING PARTIAL SURFACE FROM VOLUMETRIC DATA FOR REGISTRATION TO SURFACE TOPOLOGY IMAGE DATA" and filed on Nov. 24, 2014, which is incorporated herein by reference in its entirety.

In steps 210 and 215 (which may be performed together as opposed to serially), a navigation image is generated including (i) a virtual representation of the medical instrument, shown relative to anatomical and/or functional features of the pre-operative image data, as per the tracked position and orientation of the medical instrument, and (ii) one or more spatial annotations positioned at prescribed locations along the longitudinal axis relative to the position of the medical instrument. Each spatial annotation identifies a respective image region having a known length measure associated therewith. As illustrated in the preceding example embodiments shown in FIGS. 1A-1B, 2A-2E and 3, each spatial annotation may be configured such that the image region associated therewith is centered on the longitudinal axis and extends orthogonal to the longitudinal axis.

As shown in step 220, the annotated guidance image is then displayed (e.g. in a display window of a user interface), such that the spatial annotations enable a visual assessment of the size of anatomical and/or functional features proximal to the longitudinal axis of the medical instrument. As shown in the flow chart illustrating this example method, steps 200-210 may be repeated such that a series of navigation images are provided, thereby providing dynamic intraoperative tracking and navigation with spatial annotations identifying known length measures that are spatially correlated with the tracked position and orientation of the medical instrument.

In some embodiments, the spatial annotations are displayed in each guidance image (i.e. in each guidance image frame), at prescribed locations along the longitudinal axis that are spatially fixed relative to the tracked position and orientation of the medical instrument. In other example embodiments, however, the annotations can be displayed in a more dynamic manner.

In one example implementation, the spatial annotations may be displayed with temporal multiplexing, such that different spatial annotations are shown in different guidance images. For example, the guidance images may be displayed such that the different spatial annotations are shown in separate sequential displayed guidance images, and such that the full set of spatial annotations are sequentially cycled as a function of time.

In another example implementation, the positions of the spatial annotations along the longitudinal axis are varied as a function of time relative to the position of the medical instrument, during the display of the navigation images, such that the spatial annotations are periodically translated along the longitudinal axis when the medical instrument is detected to be at rest, or approximately at rest; e.g. when a position of the medical instrument (e.g. the position of the distal end of the medical instrument) is maintained within a prescribed spatial threshold (e.g. within ±1 mm, within ±2 mm, within ±3 mm, within ±4 mm, within ±5 mm) within a prescribed amount of time (e.g. within 1 second, within 2 seconds, within 3 seconds, within 4 seconds, or within 5 seconds).

In some example implementations, the spatial annotations may be displayed according to the detected speed of motion of the medical instrument, such that navigation images including the spatial annotations are displayed only when the speed of the medical instrument is determined to be below a pre-selected threshold. In another example implementation, the navigation images including the spatial annotations may be generated and displayed with an increased magnification when the speed of the medical instrument is below a pre-selected threshold. These example embodiments may also be implemented according to whether or not the medical instrument is detected to be at rest, or approximately at rest.

In another example implementation, the spatial annotations may be displayed such that a single spatial annotation is displayed at any given time, and where the display of a given spatial annotation is selectable via input from an operator. The input may be associated with the rotational orientation of the medical instrument relative to the longitudinal axis, such that as the medical instrument is rotated, the different spatial annotations are selectively displayed. In one example implementation, the user input may be employed to vary the known length measure associated with a spatial given annotation. For example, the length measure associated with a given spatial annotation may be varied by rotating the medical instrument about its longitudinal axis while maintaining a position of the medical instrument (e.g. the position of the distal end of the medical instrument) within a prescribed spatial threshold (e.g. within ±1 mm, within ±2 mm, within ±3 mm, within ±4 mm, or within ±5 mm).

In some example embodiments, the display of the spatial annotations may be controlled based on operator input. For example, the spatial annotations may displayed only when the a position of the medical instrument (e.g. the position of the distal end of the medical instrument) is maintained at rest or approximately at rest, e.g. within a prescribed spatial threshold (e.g. within ±1 mm, within ±2 mm, within ±3 mm, within ±4 mm, within ±5 mm) within a prescribed amount of time (e.g. within 1 second, within 2 seconds, within 3 seconds, within 4 seconds, or within 5 seconds). In other example implementations, the display of the spatial annotations may be toggled based on input received from an input device such as a foot pedal, a touch-sensitive display, input received by a mouse, keyboard or other physical input device, voice commands received through a microphone, and gesture input detected, for example, via recorded images, or via input received by a proximity sensor embedded in the system. In some example implementations, the spatial annotations may be displayed for a prescribed time interval, such as 1 second, 2 seconds, 3 seconds, 4 seconds, or 5 seconds, after receiving input triggering the display of the spatial annotations.

It will be understood that the preceding example embodiments involving surgical procedures of the spine are merely provided as illustrative examples, and that various embodiments described herein may be employed and adapted to a wide variety of medical procedures. For example, in minimally invasive spine and/or cranial surgery tube retractors are used to facilitate access to the target anatomy by gradually increasing the tube size. By tracking one or more of the tubes and showing associated spatial annotations determination of the tube sizes to be used next and overall trajectory can be made. In another example, during a biopsy procedure of a tumor typically the viable rim of the tumor is targeted. When selecting an entry point with a tracked probe or biopsy needle on the surface of the patient distalward spatial annotations shown near the tumor enable the surgeon to shift the entry point by a known distance to target the center of the viable rim.

Figure 5:
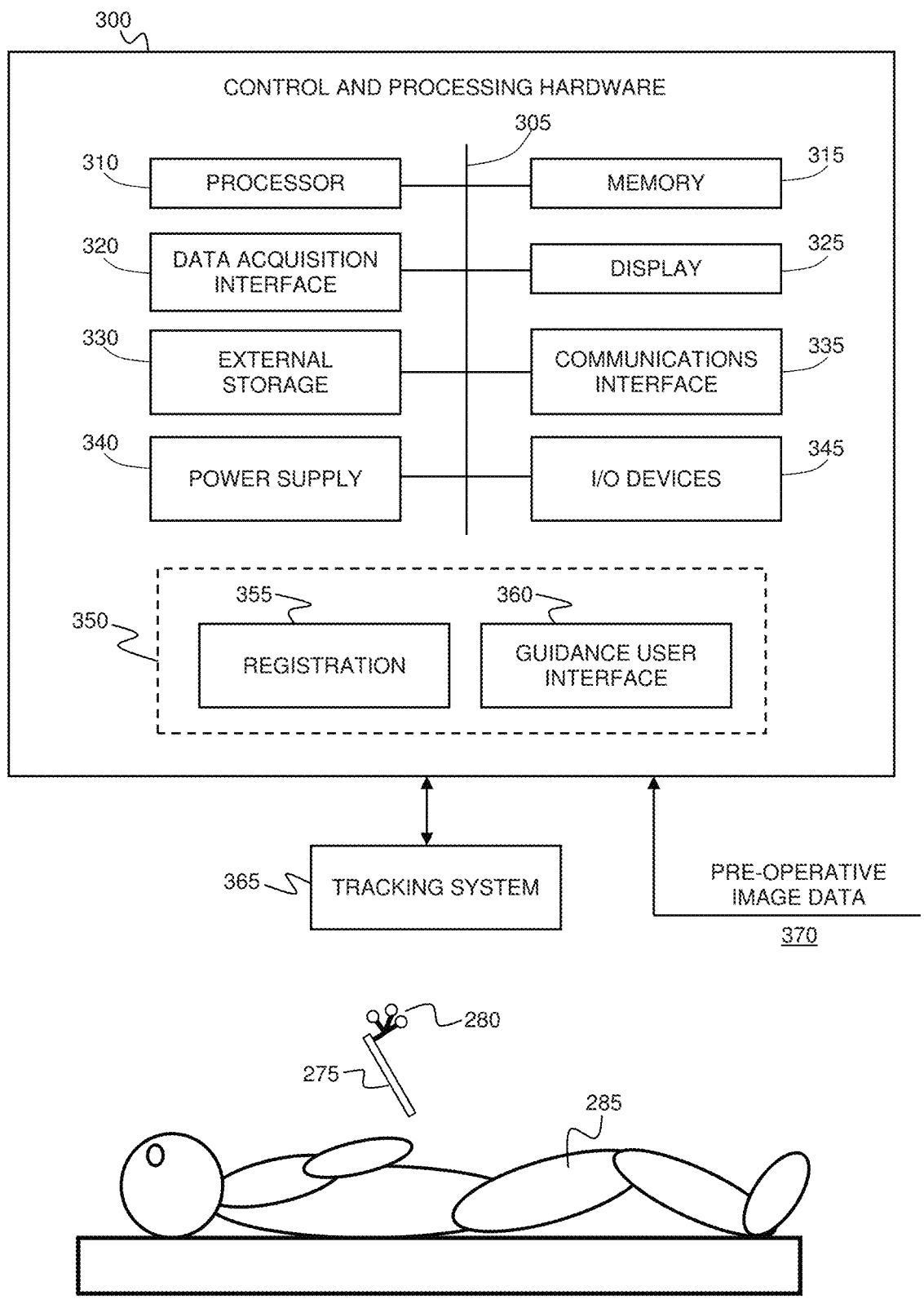
FIG. 5 is an example system for performing tracking and navigation during a medical procedure.

FIG. 5 provides a block diagram illustrating an example implementation of a system for implementing the example embodiments described above. The tracking system 365 is employed to track the position and orientation of one or more medical instruments 375, as described above. The medical instrument 375 is shown having fiducial markers 380 attached thereto, and passive or active signals emitted from the fiducial markers 380 are detected by the tracking system 365 (e.g. a stereographic tracking system employing two tracking cameras). In an alternative example embodiment, the position and orientation of a medical instrument may be tracked via a surface profile detection system, such as a structure light detection system, that is employed to detect the surface profile of a of at least portion of the medical instrument, or structure attached thereto, and to determine the position and orientation of the medical instrument via comparison of the detected surface profile with a known surface profile.

FIG. 4 provides an example implementation of control and processing hardware 300, which includes one or more processors 310 (for example, a CPU/microprocessor), bus 305, memory 315, which may include random access memory (RAM) and/or read only memory (ROM), a data acquisition interface 320, a display 325, external storage 330, one more communications interfaces 335, a power supply 340, and one or more input/output devices and/or interfaces 345 (e.g. a speaker, a user input device, such as a keyboard, a keypad, a mouse, a position tracked stylus, a position tracked probe, a foot switch, and/or a microphone for capturing speech commands).

Control and processing hardware 300 may be programmed with programs, subroutines, applications or modules 350, which include executable instructions, which when executed by the one or more processors 310, causes the system to perform one or more methods described in the present disclosure. Such instructions may be stored, for example, in memory 315 and/or other internal storage. In particular, in the example embodiment shown, registration module 355 includes executable instructions for registering pre-operative image data 370 to an intraoperative reference frame, for example, according to one of the registration methods described above. Guidance user interface module 360 includes executable instructions for displaying a user interface according to the aforementioned methods, whereby spatial annotations, having reference length measurements associated therewith, are dynamically displayed with respect to the detected position and orientation of the medical instrument.

Although only one of each component is illustrated in FIG. 4, any number of each component can be included in the control and processing hardware 300. For example, a computer typically contains a number of different data storage media. Furthermore, although bus 305 is depicted as a single connection between all of the components, it will be appreciated that the bus 305 may represent one or more circuits, devices or communication channels which link two or more of the components. For example, in personal computers, bus 305 often includes or is a motherboard. Control and processing hardware 300 may include many more or less components than those shown.

Control and processing hardware 300 may be implemented as one or more physical devices that are coupled to processor 310 through one of more communications channels or interfaces. For example, control and processing hardware 300 can be implemented using application specific integrated circuits (ASICs). Alternatively, control and processing hardware 300 can be implemented as a combination of hardware and software, where the software is loaded into the processor from the memory or over a network connection.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing tracking and navigation during a medical procedure, the method comprising:
   detecting, with a tracking system, signals from one or more fiducial markers associated with a medical instrument, the medical instrument comprising an elongate portion characterized by a longitudinal axis;
   processing the signals to determine a position and an orientation of the medical instrument;
   employing a coordinate transformation to represent pre-operative image data and the position and orientation of the medical instrument within a common reference frame; and
   generating and displaying a navigation user interface comprising:
      a virtual representation of the medical instrument;
      anatomical and/or functional features associated with the pre-operative image data;
      a plurality of virtual spatial annotations positioned at prescribed locations along the longitudinal axis relative to the position of the medical instrument, each virtual spatial annotation having a transverse spatial extent indicating a corresponding different absolute transverse length measure, the transverse spatial extent being determined in a direction orthogonal to the longitudinal axis; and
      numeric values of the different absolute transverse length measures that correspond to the spatial annotations;
      the virtual spatial annotations thereby enabling a visual representation of the size of anatomical and/or functional features proximal to the longitudinal axis.

2. The method according to claim 1 wherein at least a subset of the virtual spatial annotations are displayed at respective locations along the elongate portion of the medical instrument.

3. The method according to claim 1 wherein at least a subset of the virtual spatial annotations are displayed at respective locations that reside beyond a distal end of the medical instrument.

4. The method according to claim 3 wherein the distance, along the longitudinal axis, between each virtual spatial annotation and the distal end of the medical instrument, is selected such that when the distal end of the medical instrument contacts a bone surface at a suitable entry point associated with the medical procedure, each virtual spatial annotation is displayed proximal to a subregion of interest.

5. The method according to claim 4 wherein the subregion of interest comprises a pedicle of a spine.

6. The method according to claim 5 wherein the medical instrument is an awl.

7. The method according to claim 5 wherein the medical procedure comprises the insertion of a tool, wherein the tool is selectable according to a plurality of tool diameters, and wherein each absolute transverse length measure represents a different tool diameter, thereby permitting the selection of a suitable tool diameter by visual comparison of the virtual spatial annotations with the anatomical and/or functional features.

8. The method according to claim 7 wherein the tool is a fastener.

9. The method according to claim 8 wherein the fastener is a pedicle screw.

10. The method according to claim 1 at least two of the plurality of virtual spatial annotations are spatially distributed along the longitudinal axis.

11. The method according to claim 10 wherein each virtual spatial annotation has a different spatial extent and represents a different respective absolute transverse length measure, and wherein the virtual spatial annotations that are spatially distributed along the longitudinal axis are displayed along the longitudinal axis in an ordered configuration according to an increasing or decreasing size of the respective absolute transverse length measures.

12. The method according to claim 11 wherein the virtual spatially annotation having the largest absolute transverse length measure is displayed nearest to a proximal end of the medical instrument.

13. The method according to claim 1 further comprising generating and displaying a plurality of navigation images, each navigation image including the plurality of virtual spatial annotations, wherein the location of one or more virtual spatial annotations is varied as a function of time relative to the position of the medical instrument during the display of the plurality of navigation images.

14. The method according to claim 1 further comprising, prior to generating and presenting the navigation user interface comprising the virtual spatial annotations:
   determining a speed of the medical instrument;
   comparing the speed of the medical instrument to a pre-selected threshold; and
   determining that the speed of the medical instrument is below the pre-selected threshold.

15. The method according to claim 1 further comprising:
   determining a speed of the medical instrument;
   comparing the speed of the medical instrument to a pre-selected threshold;
   determining that the speed of the medical instrument is below the pre-selected threshold; and
   increasing a magnification of the annotations.

16. The method according to claim 1 wherein the navigation user interface includes a legend associating each virtual spatial annotation with its respective absolute transverse length measure.

17. The method according to claim 1 wherein the navigation user interface comprises a visual representation of the longitudinal axis.

18. The method according to claim 17 further comprising displaying a set of spatial graduations along the longitudinal axis.

19. The method according to claim 1 wherein the navigation user interface is a two-dimensional representation of a two-dimensional region, the two-dimensional region including the longitudinal axis.

20. The method according to claim 1 wherein the navigation user interface is a two-dimensional representation of a three-dimensional region, the three-dimensional region including the longitudinal axis.

21. The method according to claim 20 wherein the virtual spatial annotations have a circular shape.

22. The method according to claim 1 wherein each virtual spatial annotation has a different spatial extent and represents a different respective absolute transverse length measure.

23. The method according to claim 1 further comprising, prior to generating and presenting the navigation user interface comprising the virtual spatial annotations:
   determining a time duration over which the medical instrument resides within a pre-selected spatial range;
   comparing the time duration to a pre-selected time window; and
   determining that the time duration is below the pre-selected time window.

24. The method according to claim 1 further comprising:
   determining a time duration over which the medical instrument resides within a pre-selected spatial range;
   comparing the time duration to a pre-selected time window;
   determining that the time duration is below the pre-selected time window; and
   increasing a magnification of the annotations.

25. A method of performing tracking and navigation during a medical procedure, the method comprising:
   detecting, with a tracking system, signals from one or more fiducial markers associated with a medical instrument, the medical instrument comprising an elongate portion characterized by a longitudinal axis;
   processing the signals to determine a position and an orientation of the medical instrument;
   employing a coordinate transformation to represent pre-operative image data and the position and orientation of the medical instrument within a common reference frame; and
   generating and displaying a navigation user interface comprising:
      anatomical and/or functional features associated with the pre-operative image data;
      a virtual spatial annotation positioned at a prescribed location along the longitudinal axis relative to the position of the medical instrument, the virtual spatial annotation having a transverse spatial extent indicating a corresponding absolute transverse length measure, the transverse spatial extent being determined in a direction orthogonal to the longitudinal axis; and
      a numeric value of the absolute transverse length measure that corresponds to the spatial annotation;
   the virtual spatial annotation thereby enabling a visual assessment of the size of anatomical and/or functional features proximal to the longitudinal axis.

26. A method of performing tracking and navigation during a medical procedure, the method comprising:
   detecting, with a tracking system, signals from one or more fiducial markers associated with a medical instrument, the medical instrument comprising an elongate portion characterized by a longitudinal axis;
   processing the signals to determine a position and an orientation of the medical instrument;
   employing a coordinate transformation to represent pre-operative image data and the position and orientation of the medical instrument within a common reference frame; and
   generating and displaying a navigation user interface comprising:
      anatomical and/or functional features associated with the pre-operative image data;
      a plurality of virtual spatial annotations positioned at prescribed locations along the longitudinal axis relative to the position of the medical instrument, each virtual spatial annotation having a transverse spatial extent indicating a corresponding different absolute transverse length measure, the transverse spatial extent being determined in a direction orthogonal to the longitudinal axis; and
      numeric values of the different absolute transverse length measures that correspond to the spatial annotations;
   the virtual spatial annotations thereby enabling a visual assessment of the size of anatomical and/or functional features proximal to the longitudinal axis.

* * * * *